(12) United States Patent
Someya et al.

(10) Patent No.: US 10,376,174 B2
(45) Date of Patent: Aug. 13, 2019

(54) ELECTRODE AND METHOD FOR MANUFACTURING ELECTRODE

(71) Applicants: Takao Someya, Tokyo (JP); Tsuyoshi Sekitani, Osaka (JP); Kazunori Kuribara, Tsukuba-shi, Ibaraki (JP); TORAY INDUSTRIES, INC., Tokyo (JP)

(72) Inventors: Takao Someya, Tokyo (JP); Tsuyoshi Sekitani, Osaka (JP); Kazunori Kuribara, Tsukuba (JP); Ryuta Tamiya, Otsu (JP); Masataka Nakamura, Otsu (JP)

(73) Assignees: Takao Someya, Tokyo (JP); Tsuyoshi Sekitani, Osaka (JP); Kazunori Kuribara, Tsukuba-Shi, Ibaraki (JP); TORAY INDUSTRIES, INC., Tokyo (JP)

( * ) Notice: Subject to any disclaimer, the term of this patent is extended or adjusted under 35 U.S.C. 154(b) by 405 days.

(21) Appl. No.: 15/111,647

(22) PCT Filed: Feb. 5, 2015

(86) PCT No.: PCT/JP2015/053240
§ 371 (c)(1),
(2) Date: Jul. 14, 2016

(87) PCT Pub. No.: WO2015/119197
PCT Pub. Date: Aug. 13, 2015

(65) Prior Publication Data
US 2016/0331261 A1 Nov. 17, 2016

(30) Foreign Application Priority Data
Feb. 6, 2014 (JP) .................. 2014-021782

(51) Int. Cl.
*A61B 5/04* (2006.01)
*A61B 5/0478* (2006.01)

(52) U.S. Cl.
CPC ........ *A61B 5/0478* (2013.01); *A61B 5/04001* (2013.01)

(58) Field of Classification Search
CPC ....... C08L 83/04; A61B 5/00; A61B 5/04001; A61B 5/04002; A61B 5/0476; A61B 5/0478
See application file for complete search history.

(56) References Cited

U.S. PATENT DOCUMENTS 4,770,968 A * 9/1988 Georges .............. C08F 290/068
430/109.3
5,384,340 A * 1/1995 Hara .................... C08G 77/388
522/170

(Continued)

FOREIGN PATENT DOCUMENTS

JP 2005-36051 A 2/2005
JP 3676337 B2 7/2005

(Continued)

OTHER PUBLICATIONS

Park Jaewon et al., Micropatterning of poly(dimethylsiloxane) using a photoresist liftoff technique for selective electrical insulation of microelectrode arrays, May 20, 2009, JMicromech Microeng, 19: 65016, Whole Document.*

(Continued)

*Primary Examiner* — Eun Hwa Kim
(74) *Attorney, Agent, or Firm* — Birch, Stewart, Kolasch & Birch LLP

(57) ABSTRACT

In order to provide an electrode equipped with an insulating wall having excellent patterning properties as well as excellent biocompatibility, there is provided an electrode including, on a substrate, an electrode element; and an insulating (Continued)

wall formed around the electrode element, constituted of a polysiloxane compound (component A) having, per molecule, two or more functional groups selected from the group consisting of a (meth)acryloyl group, a styrenic vinyl group, a vinyl ester group, a maleic acid ester group and a maleimide group, and formed from a polymer obtained by reaction of the functional groups.

11 Claims, 6 Drawing Sheets

(56) References Cited

U.S. PATENT DOCUMENTS

| | | | |
|---|---|---|---|
| 2005/0175819 A1* | 8/2005 | Kobayashi | G03G 15/1625 428/195.1 |
| 2006/0223964 A1* | 10/2006 | Lai | A61L 27/18 528/32 |
| 2007/0080346 A1* | 4/2007 | Kim | G02F 1/136227 257/40 |
| 2007/0128420 A1* | 6/2007 | Maghribi | A61L 27/48 428/221 |
| 2009/0228066 A1 | 9/2009 | Hirata et al. | |
| 2009/0234089 A1* | 9/2009 | Ueyama | C08F 8/42 526/279 |
| 2012/0277834 A1* | 11/2012 | Mercanzini | A61B 5/04001 607/62 |
| 2013/0109776 A1 | 5/2013 | Sawada et al. | |

FOREIGN PATENT DOCUMENTS

| | | |
|---|---|---|
| JP | 2006-212133 A | 8/2006 |
| JP | 4038685 B2 | 1/2008 |
| JP | 2009-45368 A | 3/2009 |
| JP | 2013-512062 A | 4/2013 |
| JP | 2013-140229 A | 7/2013 |
| WO | WO 2011/067297 A1 | 6/2011 |
| WO | WO 2012/088398 A2 | 6/2012 |

OTHER PUBLICATIONS

Japanese Notice of Allowance for Japanese Application No. 2015-512949, dated Dec. 5, 2017, including an English translation.
"Silicones," Encyclopedia of Polymer Science and Technology, vol. 11, Wiley, US, Apr. 15, 2003, pp. 765-841, XP007918236.
Extended European Search Report, dated Aug. 9, 2017, for European Application No. 15746120.3.
Gelest, Inc., "Reactive Silicones: Forging New Polymer Links," URL:http://www.gelest.com/company/pdfs/reactivesilicones.pdf, 2004, pp. 1-56 (59 pages total), XP002470135.
Delivopoulos et al., "Evaluation of negative photo-patternable PDMS for the encapsulation of neural electrodes", Proceedings of the 5th International IEEE EMBS Conference on Neural Engineering, Apr. 27, 2011-May 1, 2011, Cancun, Mexico, pp. 490-494.
International Search Report for PCT/JP2015/053240 (PCT/ISA/210) dated Apr. 14, 2015.
Park et al., "Micropatterning of poly(dimethylsiloxane) using a photoresist lift-off technique for selective electrical insulation of microelectrode arrays", J Micromech Microeng., 19: 65016, May 20, 2009, 18 pages.
Written Opinion of the International Searching Authority for PCT/JP2015/053240 (PCT/ISA/237) dated Apr. 14, 2015.

\* cited by examiner

45mV

23mV

ELECTRODE AND METHOD FOR MANUFACTURING ELECTRODE

TECHNICAL FIELD

The present invention relates to an electrode and a method for manufacturing an electrode.

Priority is claimed on Japanese Patent Application No. 2014-021782, filed Feb. 6, 2014, the content of which is incorporated herein by reference.

BACKGROUND ART

In the field of medicine, in order to detect electrical signals such as brain waves output from biological tissues, electrodes to be used by being attached to a living body or being embedded in the living body have been utilized. As such an electrode, a pin support-shaped electrode array inserting a plurality of electrode elements composed of platinum or gold into the biological tissue has been known (for example, Patent Document 1). However, since such a highly invasive method imposes a heavy burden on the living body, there has been a demand for a measurement method with fewer burdens.

Accordingly, minimally invasive methods that do not insert the electrode elements into the living body have been developed. For example, in Patent Document 2, an electrode realizing minimal invasion by using a fine metal wire as the electrode element has been described. For example, although an electrode element made of a metal such as platinum or gold is basically harmless to the human body, when being brought into direct contact with the body tissues or cells, a defense reaction (inflammatory reaction) occurs between the electrode element and the tissue due to the antibody response of biological cells. For this reason, it is difficult to observe biological information for a prolonged period. In addition, there is a problem of heavy damage to the living body due to friction when a hard metal is rubbed inside the soft body.

In order to prevent such a problem, it is considered to place a material having biocompatibility between the electrode element and the biological tissue, thereby preventing the direct contact between the electrode element and the biological tissue.

However, in the electrode in which a plurality of electrode elements are arranged, there is a problem in that sensitivity is lowered due to the occurrence of leakage of signals between the electrode elements (crosstalk). Therefore, in order to obtain the electrical signals in the body with high sensitivity and high accuracy, it is necessary to provide an insulating wall between the electrode elements. Since this type of insulating wall also comes into contact with the living body, it is preferably formed of a highly biocompatible material, and insulating walls using silicone elastomers have been studied.

For example, in Non-Patent Document 1, a technique for forming an insulating wall made of silicone around the electrode elements has been described. The insulating wall made of silicone is obtained by coating an upper portion of the electrode element on the electrode substrate with a photoresist, spin-coating a thermosetting silicone prepolymer thereon, followed by heating to cure a polysiloxane compound, and then removing the photoresist. In Non-Patent Document 2, formation of an insulating portion of the electrode through a photolithography method employing photopolymerization by spin-coating a polysiloxane compound with a terminal vinyl ether group on the electrode substrate has also been described.

CITATION LIST

Patent Documents

[Patent Document 1] Published Japanese Translation No. 2013-512062 of the PCT International Publication
[Patent Document 2] Japanese Unexamined Patent Application, First Publication No. 2006-212133

Non-Patent Documents

[Non-Patent Document 1] J Micromech Microeng. 2009 May 20; 19: pp. 65016.
[Non-Patent Document 2] Neural Engineering (NER), 2011 5th International IEEE/EMBS Conference on Date Apr. 27, 2011-May 1, 2011 pp. 490-494.

SUMMARY OF INVENTION

Technical Problem

However, the thermosetting polysiloxane compound described in Non-Patent Document 1 has a problem in terms of productivity since it takes a long time to cure. The polysiloxane compound having a terminal vinyl ether group described in Non-Patent Document 2 is considered to have a problem in patterning properties from the viewpoint that the radical polymerization reaction hardly proceeds.

The present invention has an object of providing an electrode including an insulating wall having excellent patterning properties as well as excellent biocompatibility.

Solution to Problem

An electrode according to an embodiment of the present invention in order to solve the above problems includes, on a substrate, an electrode element, and an insulating wall formed around the electrode element, constituted of a polysiloxane compound (component A) having, per molecule, two or more functional groups selected from the group consisting of a (meth)acryloyl group, a styrenic vinyl group, a vinyl ester group, a maleic acid ester group and a maleimide group, and formed from a polymer obtained by reaction of the functional groups.

A method for manufacturing an electrode according to an embodiment of the present invention includes a step of placing an electrode element on a substrate, a step of placing, around the electrode element, a photocurable material including a polysiloxane compound (component A) having, per molecule, two or more functional groups selected from the group consisting of a (meth)acryloyl group, a styrenic vinyl group, a vinyl ester group, a maleic acid ester group and a maleimide group, and a photoradical polymerization initiator, and a step of forming the insulating wall by irradiating an electromagnetic wave to the photocurable material to cure.

Advantageous Effects of Invention

By the electrode in accordance with an embodiment of the present invention, it is possible to provide an electrode having an insulating wall with excellent patterning properties and excellent biocompatibility.

DESCRIPTION OF EMBODIMENTS

Figure 1:
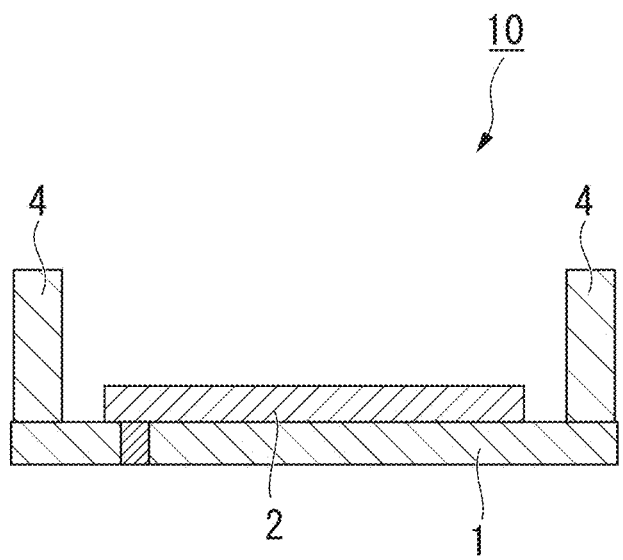
FIG. 1 is a schematic sectional view of an electrode according to an embodiment of the present invention.

FIG. 1 is a diagram schematically showing the cross section of an electrode according to an embodiment of the present invention. An electrode 10 shown in FIG. 1 includes, on a substrate 1, an electrode element 2, and an insulating wall 4 formed around the electrode element 2.

The substrate 1 of the electrode 10 is not particularly limited, but preferably has the strength to serve as a base of the electrode 10, and maintains the flexibility. More specifically, it is preferable that the Young's modulus is from 0.1 GPa to 10 GPa. As the substrate, for example, polyimide (PI), polyethylene terephthalate (PET), polyethylene naphthalate (PEN), polytetrafluoroethylene (Teflon (registered trademark)), and the like can be used.

The thickness of the substrate 1 is preferably thinner than the thickness of the insulating wall 4 described later. Since the insulating wall 4 to be described later is generally soft with low Young's modulus, by making the thickness of the substrate 1 thinner than the thickness of the insulating wall 4, it is possible to ensure the flexibility of the electrode 10. More specifically, the thickness of the substrate 1 is preferably at least 1 μm and not more than 50 μm. If the thickness of the substrate 1 is less than 1 μm, the strength is not sufficient to serve as a base for the electrode 10, and the overall mechanical strength drops. If the thickness of the substrate 1 is thicker than 50 μm, it is difficult to secure sufficient flexibility for the electrode. Therefore, for example, the capacity to follow complex shapes such as those of the brains reduces.

The material for the electrode element 2 is not particularly limited, and metals such as gold or platinum, organic conductive materials such as PEDOT/PSS, carbon nanomaterials, conductive materials having biocompatibility, or the like can be used.

Here, the carbon nanomaterials refer to those constituted of carbon atoms and in which the carbon atoms that are serving as components and structured into a nanometer size (for example, one CNT) are joined with each other by van der Waals force, such as carbon nanotubes, carbon nanofibers (those carbon fibers with a diameter of 10 nm or less), carbon nanohorns, and fullerenes. A fine carbon nanomaterial with a diameter of 10 nm or less exhibits favorable dispersibility in water.

In order to enhance the sensitivity of the electrode element 2, it is preferable to use a highly conductive metal such as gold and platinum. In order to prevent adverse effects on the living body by the defense reaction, friction, and the like, as described later, it is preferable to coat the electrode element 2 with a biological buffer layer 3 exhibiting biocompatibility.

The insulating wall 4 includes a polysiloxane compound having, per molecule, two or more functional groups selected from the group consisting of a (meth)acryloyl group, a styrenic vinyl group, a vinyl ester group, a maleic acid ester group and a maleimide group as a constituent, and is formed from a polymer obtained by reaction of the functional groups. Hereinafter, in the present specification, the "functional groups selected from the group consisting of a (meth)acryloyl group, a styrenic vinyl group, a vinyl ester group, a maleic acid ester group and a maleimide group" will be collectively referred to as "polymerizable functional groups". In addition, a "polysiloxane compound having, per molecule, two functional groups selected from the group consisting of a (meth)acryloyl group, a styrenic vinyl group, a vinyl ester group, a maleic acid ester group and a maleimide group" will be referred to as a "component A".

The polysiloxane compound represents a compound having a repeating structure (r) denoted by the following chemical formula (r) $R^a$ and $R^b$ are monovalent organic groups, and $R^a$ and $R^b$ may be the same or different for each repeating structure (r)).

The number of the polymerizable functional groups of the component A is not particularly limited as long as it is two or more per molecule, but is preferably 2 per molecule from the viewpoint that a more flexible polymer (with a low Young's modulus) can be easily obtained. The component A may have the polymerizable functional groups at any position in the molecular chain, although a structure having the polymerizable functional groups at both ends of the molecular chain is particularly preferred. Two or more polymerizable functional groups of the component A molecule may be the same or may be different from each other.

The polymerizable functional groups are most preferably (meth)acryloyl groups. This is because (meth)acryloyl groups exhibit high polymerizability.

The number average molecular weight of the component A is preferably at least 6,000. When the number average molecular weight of the component A is in this range, a polymer particularly excellent in flexibility and also excellent in mechanical properties such as bending resistance can be obtained. The number average molecular weight of the component A is preferably at least 8,000, more preferably in the range of 8,000 to 100,000, still more preferably in the range of 9,000 to 70,000, and most preferably in the range of 10,000 to 50,000, since a polymer with even more excellent mechanical properties such as bending resistance can be obtained. When the number average molecular weight of the component A is too small, mechanical properties such as bending resistance tend to decrease. When the number average molecular weight of the component A is too large, there is a tendency that flexibility and transparency decrease.

Here, the number average molecular weight of a compound is defined as a number average molecular weight in terms of polystyrene as measured with a gel permeation chromatography method (GPC method) using chloroform as a solvent. Also for the mass average molecular weight and the dispersion degree (value obtained by dividing the mass average molecular weight by the number average molecular weight), values measured in the same manner are used.

The dispersion degree (value obtained by dividing the mass average molecular weight by the number average molecular weight) of the component A is preferably equal to or less than 6, more preferably equal to or less than 3, still more preferably equal to or less than 2, and most preferably equal to or less than 1.5. When the dispersion degree of the component A is small, the compatibility with other components improves, and the advantages such as the reduction of the impurities contained in the obtained polymer, and the reduction of shrinkage associated with the polymer molding are brought about.

As the component A, a compound having a structure represented by the following general formula (A1) is preferred.

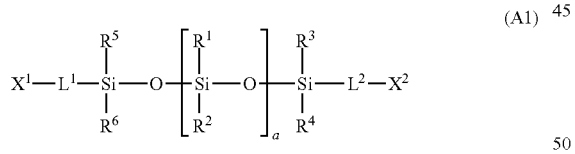

(A1)

In the general formula (A1), each of $X^1$ and $X^2$ independently represents a functional group selected from the group consisting of a (meth)acryloyl group, a styrenic vinyl group, a vinyl ester group, a maleic acid ester group and a maleimide group. Each of $R^1$ to $R^6$ independently represents a substituent group selected from hydrogen, an alkyl group of 1 to 20 carbon atoms, a phenyl group, and a fluoroalkyl group of 1 to 20 carbon atoms. Each of $L^1$ and $L^2$ independently represents a divalent group. "a" is the number of siloxane repeating units represented by an integer of 1 to 3,000.

In the general formula (A1), $X^1$ and $X^2$ are most preferably (meth)acryloyl groups.

In the general formula (A1), hydrogen, an alkyl group, and a fluoroalkyl group may be used as preferred specific examples of $R^1$ to $R^6$. Examples of the alkyl group include alkyl groups of 1 to 20 carbon atoms, such as a methyl group, an ethyl group, a propyl group, an isopropyl group, a butyl group, a t-butyl group, a decyl group, a dodecyl group and an octadecyl group. As the fluoroalkyl group, a fluoroalkyl group of 1 to 20 carbon atoms, such as a phenyl group, a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a tetrafluoropropyl group, a pentafluoropropyl group, a tetradecafluorooctyl group, a pentadecafluorooctyl group, an octadecafluorodecyl group, and a nonadecafluorodecyl group, and the like can be mentioned. From the viewpoint of providing favorable mechanical properties to the polymer, hydrogen and a methyl group are preferred, and a methyl group is most preferred. In other words, as A1, a compound having a polydimethylsiloxane structure is most preferred.

In the general formula (A1), as $L^1$ and $L^2$, an alkyl group or fluoroalkyl group having 1 to 20 carbon atoms is preferred. Among the various groups, groups represented by any one of the following formulas (LE1) to (LE12) are preferred, groups represented by the following formula (LE1), (LE3), (LE9) or (LE11) are more preferred, groups represented by the following formula (LE1) or (LE3) are still more preferred, and groups represented by the following formula (LE1) are most preferred. When the groups are represented by these chemical formulas, the compounds of general formula (A1) can be easily obtained in high purity. The following formula (LE1) to (LE12) are depicted in such a manner that a terminal to be bound to the polymerizable functional group $X^1$ or $X^2$ is on the left hand side, while a terminal to be bound to a silicon atom is on the right hand side.

—OCH$_2$CH$_2$CH$_2$—                    (LE1)

—NHCH$_2$CH$_2$CH$_2$—                    (LE2)

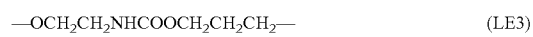

—OCH$_2$CH$_2$NHCOOCH$_2$CH$_2$CH$_2$—            (LE3)

—OCH$_2$CH$_2$NHCONHCH$_2$CH$_2$CH$_2$—           (LE4)

—OCH$_2$CH$_2$CH$_2$CH$_2$—                  (LE5)

—NHCH$_2$CH$_2$CH$_2$CH$_2$—                 (LE6)

—OCH$_2$CH$_2$NHCOOCH$_2$CH$_2$CH$_2$CH$_2$—         (LE7)

—OCH$_2$CH$_2$NHCONHCH$_2$CH$_2$CH$_2$CH$_2$—        (LE8)

—OCH$_2$CH$_2$OCH$_2$CH$_2$CH$_2$—               (LE9)

—NHCH$_2$CH$_2$OCH$_2$CH$_2$CH$_2$—              (LE10)

—OCH$_2$CH$_2$NHCOOCH$_2$CH$_2$OCH$_2$CH$_2$CH$_2$—     (LE11)

—OCH$_2$CH$_2$NHCONHCH$_2$CH$_2$OCH$_2$CH$_2$CH$_2$—    (LE12)

In the general formula (A1), the value of "a" is preferably at least 80, more preferably at least 100, still more preferably from 100 to 1,400, still more preferably from 120 to 950, and still more preferably from 130 to 700. When all of $R^1$ to $R^6$ are methyl groups, "a" is preferably from 80 to 1,500, more preferably from 100 to 1,400, still more preferably from 120 to 950, and still more preferably from 130 to 700.

The polymer for forming the insulating wall 4 may be a copolymer of the component A and a component M which is a polysiloxane compound having, per molecule, one functional group (polymerizable functional group) selected from the group consisting of a (meth)acryloyl group, a styrenic vinyl group, a vinyl ester group, a maleic acid ester group and a maleimide group. By preparing a copolymer with the component M having only one polymerizable functional group per molecule, the crosslinking density is reduced and the degree of freedom of the polymer is increased, as a result of which a more flexible insulating wall with a low Young's modulus can be formed.

The number average molecular weight of the component M is preferably from 300 to 120,000. By ensuring that the number average molecular weight of the component M is within this range, a polymer excellent in flexibility and also excellent in mechanical properties such as bending resistance can be obtained. The number average molecular weight of the component M is preferably at least 500, more preferably in the range from 1,000 to 25,000, and still more preferably in the range from 5,000 to 15,000. When the number average molecular weight of the component M is too small, mechanical properties such as bending resistance and shape recovery property tend to be low. When the number average molecular weight of the component M is too large, there is a tendency that the flexibility is lowered.

The component M preferably has a structure represented by the following general formula (M1).

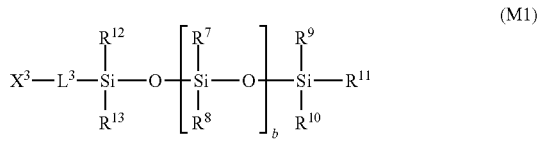
(M1)

In the general formula (M1), $X^3$ represents a functional group selected from the group consisting of a (meth)acryloyl group, a styrenic vinyl group, a vinyl ester group, a maleic acid ester group and a maleimide group. Each of $R^7$ to $R^{13}$ independently represents a substituent group selected from hydrogen, an alkyl group of 1 to 20 carbon atoms, a phenyl group, and a fluoroalkyl group of 1 to 20 carbon atoms. $L^3$ represents a divalent group. "b" is the number of siloxane repeating units, and represents an integer of 0 to 1,400.

In the general formula (M1), as $X^3$, a (meth)acryloyl group is the most preferred because it has the highest polymerizability.

In the general formula (M1), preferred specific examples of $R^7$ to $R^{13}$ are the same as those mentioned as preferred examples of $R^1$ to $R^6$ in the general formula (1) described above. Preferred specific examples of $L^3$ are the same as those mentioned as preferred examples of $L^1$ and $L^2$ in the general formula (1) described above.

In the general formula (M1), b represents an integer of 1 to 1,400. "b" is preferably at least 3, more preferably at least 10, still more preferably from 10 to 500, still more preferably from 30 to 300, and most preferably from 50 to 200. In particular, when all of $R^7$ to $R^{13}$ are methyl groups, "b" is preferably from 3 to 700, more preferably from 10 to 500, still more preferably from 30 to 300, and still more preferably from 50 to 200.

It is more preferable that the polymerizable functional group of the component M be copolymerizable with the polymerizable functional group of the component A, since the polymer with favorable mechanical properties can be easily obtained. Since a polymer having favorable surface properties can be easily obtained by uniformly copolymerizing the component M and the component A, it is more preferable that the component M have a common polymerizable functional group with the component A.

The mass ratio of the component A and the component M contained in the polymer constituting the insulating wall 4 is preferably such that the component M is from 5 to 200 parts by mass, more preferably from 7 to 150 parts by mass, and still more preferably from 10 to 100 parts by mass, with respect to 100 parts by mass of the component A. By ensuring that an appropriate amount of the component M is included in the polymer, the crosslinking density is reduced to increase the degree of freedom of the polymer, and it is possible to realize a moderately soft polymer with a low Young's modulus. On the other hand, when the content of the component M is less than 5 parts by mass with respect to 100 parts by mass of the component A, there is a tendency that the crosslinking density is increased and the polymer becomes hard. When the content of the component M is more than 200 parts by mass with respect to 100 parts by mass of the component A, the polymer tends to become too soft.

In the polymer constituting the insulating wall 4, for the component M, only one type of component may be used or two or more types of components may be used in combination.

It is also preferable that the polymer forming the insulating wall 4 is a copolymer obtained by copolymerizing, with the component A or a copolymer of the component A and the component M, a component B which is a compound having a fluoroalkyl group and one or more functional groups (polymerizable functional groups), per molecule, selected from the group consisting of a (meth)acryloyl group, a styrenic vinyl group, a vinyl ester group, a maleic acid ester group and a maleimide group. The component B has a property of water and oil repellency by the reduction of the critical surface tension resulting from the fluoroalkyl group, thereby having the effect of preventing the polymer surface from being contaminated by the components such as lipids.

The component B has an effect of providing a properties which is soft and also excellent in mechanical properties, such as bending resistance to an electrode. Preferred specific examples of the fluoroalkyl groups of the component B are fluoroalkyl groups of 1 to 20 carbon atoms, such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a tetrafluoropropyl group, a pentafluoropropyl group, a tetradecalluorooctyl group, a pentadecafluorooctyl group, an octadecafluorodecyl group, and a nonadecafluorodecyl group. Fluoroalkyl groups having 2 to 8 carbon atoms, for example, a trifluoroethyl group, a tetrafluoropropyl group, a hexafluoroisopropyl group, an octafluoropentyl group, and a dodecafluorooctyl group are more preferred, and a trifluoroethyl group is most preferred.

The polymerizable functional group of the component B is most preferably a (meth)acryloyl group.

Since the effect of obtaining a flexible electrode provided with excellent wearing feeling and excellent mechanical properties such as bending resistance is large, a (meth) acrylic acid fluoroalkyl ester is most preferred as the component B. Specific examples of the (meth)acrylic acid fluoroalkyl esters include trifluoroethyl (meth)acrylate, tetrafluoroethyl (meth)acrylate, trifluoropropyl (meth)acrylate, tetrafluoropropyl (meth)acrylate, pentafluoropropyl (meth)acrylate, hexafluorobutyl (meth)acrylate, hexafluoroisopropyl (meth)acrylate, heptafluorobutyl (meth)acrylate, octafluoropentyl (meth)acrylate, nonafluoropentyl (meth)acrylate, dodecafluoropentyl (meth)acrylate, dodecafluoroheptyl (meth)acrylate, dodecafluorooctyl (meth)acrylate, and tridecafluoroheptyl (meth)acrylate. Trifluoroethyl (meth)acrylate, tetrafluoroethyl (meth)acrylate, hexafluoroisopropyl (meth)acrylate, octafluoropentyl (meth)acrylate, dodecafluorooctyl (meth)acrylate are preferably used, and trifluoroethyl (meth)acrylate is most preferred.

The preferred content of the component B in the copolymer is preferably from 10 to 500 parts by mass, more preferably from 20 to 400 parts by mass, and still more preferably from 20 to 200 parts by mass, with respect to 100 parts by mass of the component A.

In the polymer constituting the insulating wall 4, for the component B, only one type of component may be used or two or more types of components may be used in combination.

As the copolymer to be used for the insulating wall 4, a copolymer obtained by further copolymerizing another component (hereinafter, referred to as a "component C") having the same polymerizable functional groups as those of the component A, the component M and the component B described above may be used. As the component C, components that lower the glass transition point of the copolymer to room temperature or to 0° C. or less are preferred. Since these components reduce the cohesive energy, the effect of providing the copolymer with rubber elasticity and softness can be achieved.

Examples of the component C to lower the glass transition point of the copolymer to room temperature or to 0° C. or less include (meth)acrylic acid alkyl esters, and preferably (meth)acrylic acid alkyl esters having an alkyl group of 1 to 20 carbon atoms. Specific examples thereof include methyl (meth)acrylate, ethyl (meth)acrylate, n-propyl (meth)acrylate, n-butyl (meth)acrylate, tert-butyl (meth)acrylate, isobutyl (meth)acrylate, n-hexyl (meth)acrylate, n-octyl (meth)acrylate, 2-ethylhexyl (meth)acrylate, n-heptyl (meth)acrylate, n-nonyl (meth)acrylate, n-decyl (meth)acrylate, isodecyl (meth)acrylate, n-lauryl (meth)acrylate, tridecyl (meth)acrylate, n-dodecyl (meth)acrylate, cyclopentyl (meth)acrylate, cyclohexyl (meth)acrylate, and n-stearyl (meth)acrylate. Among these, n-butyl (meth)acrylate, n-octyl (meth)acrylate, n-lauryl (meth)acrylate and n-stearyl (meth)acrylate are more preferred. Of these, (meth)acrylic acid alkyl esters with an alkyl group of 1 to 10 carbon atoms are still more preferred.

In order to improve the mechanical properties, it is preferable to conduct the copolymerization using, for example, aromatic vinyl compounds such as styrene, tert-butylstyrene, and α-methylstyrene as the component C.

In order to improve the dimensional stability of the polymer, it is preferable to conduct the copolymerization using, for example, ethylene glycol dimethacrylate, diethylene glycol dimethacrylate, triethylene glycol dimethacrylate, polyethylene glycol dimethacrylate, trimethylolpropane trimethacrylate, pentaerythritol tetramethacrylate, bisphenol A dimethacrylate, vinyl methacrylate, acryl methacrylate and acrylates corresponding to these methacrylates, divinylbenzene, triallyl isocyanurate, and the like as the component C.

In the polymer constituting the insulating wall 4, for the component C, only one type of component may be used or two or more types of components may be used in combination.

The insulating wall 4 preferably has a degree of crosslinking in the range from 2.0 to 18.3. The degree of crosslinking is expressed by the following formula (Q1).

$$\text{Degree of crosslinking} = \frac{\sum_{n=1}^{\infty} \{Qn \times (n-1)\}}{\sum_{n=1}^{\infty} Wn} \quad (Q1)$$

In the above formula (Q1), Qn represents the total amount of the monomers having n polymerizable functional groups, per molecule, in millimoles, and Wn represents the total mass (kg) of the monomers having n polymerizable groups per molecule. If the molecular weight of the monomer has a distribution, the amount in millimoles will be calculated using the number average molecular weight.

When the degree of crosslinking of the insulating wall 4 becomes smaller than 2.0, it becomes too soft to be easily damaged, whereas when the degree becomes greater than 18.3, there is a tendency that it becomes too hard to deteriorate the adhesiveness to the living body. The degree of crosslinking is more preferably from 3.5 to 16.0, still more preferably from 8.0 to 15.0, and most preferably from 9.0 to 14.0.

The insulating wall 4 preferably has a Young's modulus of 0.5 MPa to 2,000 MPa, and more preferably from 1 MPa to 1,000 MPa. By ensuring that the insulating wall 4 have a hardness of this degree, it becomes possible for the insulating wall 4 to support the substrate 1 and the biological buffer layer 3 like a backbone, and the mechanical strength of the electrode can be increased.

The tensile elongation (fracture elongation) of the insulating wall 4 is preferably at least 50%, more preferably at least 150%, still more preferably at least 170%, still more preferably at least 200%, still more preferably at least 300%, and particularly preferably at least 400%. The tensile elongation of the insulating wall 4 is preferably not more than 3,000%, more preferably not more than 2,500%, still more preferably not more than 2,000%, still more preferably not more than 1,500%, and most preferably not more than 1,000%. When the tensile elongation is small, it is not preferable since the insulating wall becomes fragile. When the tensile elongation is too large, it is not preferable since there is a tendency that the insulating wall is easily deformed.

From the viewpoint of oxygen supply from the atmosphere to the living body to which the electrode 10 will be mounted, the material of the insulating wall 4 preferably has high oxygen permeability. The oxygen permeability coefficient [$\times 10^{-11}$ (cm$^2$/sec) mLO$_2$/(mL·hPa)] is preferably at least 50, more preferably at least 100, still more preferably at least 200, and most preferably at least 300. The oxygen permeability coefficient is preferably equal to or less than 2,000, more preferably equal to or less than 1,500, still more preferably equal to or less than 1,000, and most preferably equal to or less than 700. When the oxygen permeability is excessively increased, other physical properties such as mechanical properties may be adversely affected.

The resistivity of the insulating wall 4 is preferably equal to or greater than 1 kΩm, more preferably equal to or greater than 10 kΩm, and still more preferably equal to or greater than 100 kΩm. Since such a high resistance value is required for the insulating wall 4, the water content is preferably low. The water content of the insulating wall 4 is preferably equal to or less than 10% by mass, more preferably equal to or less than 3% by mass, and still more preferably equal to or less than 1% by mass. Here, the water content can be obtained, from the mass of a film-shaped test piece in a dry state and the mass thereof in a wet state with a borate buffer, by the formula: [{(mass in the wet state)−(mass in the dry state)}/(mass in the wet state)]×100.

Here, the term "wet state" refers to a state in which the sample is immersed for 24 hours or more in pure water or borate buffer at room temperature (25° C.). Measurements of physical property values in the wet state are conducted as soon as possible after collecting the samples from the pure water or borate buffer and wiping off the surface water. The dry state refers to a state achieved by vacuum drying a sample in a wet state for 16 hours at 40° C. The degree of vacuum in the vacuum drying is equal to or less than 2 hPa. Measurements of physical property values in the dry state are conducted as soon as possible after the vacuum drying. The borate buffer is a "salt solution" described in Example 1 of Published Japanese Translation No. 2004-517163 of the PCT International Publication. More specifically, it is an aqueous solution obtained by dissolving 8.48 g of sodium chloride, 9.26 g of boric acid, 1.0 g of sodium borate (sodium tetraborate decahydrate), and 0.10 g of ethylenediaminetetraacetic acid in pure water and made up to 1,000 mL.

Arrangement of the insulating wall 4 is not particularly limited as long as the individual electrode elements are surrounded, and examples thereof include a square lattice arrangement, a honeycomb lattice arrangement, a random arrangement, and a rectangular lattice arrangement. The square lattice arrangement is preferable from the viewpoint of ease of production. A honeycomb lattice arrangement is preferable in view of the mechanical strength. The insulating wall may be inclined and needs not to be erected perpendicularly with respect to the substrate.

The electrode 10 can be produced by a production method including a step of placing an electrode element 2 on a substrate 1, a step of placing, around the electrode element 2, a photocurable material including a polysiloxane compound (component A) having, per molecule, two or more functional groups selected from the group consisting of a (meth)acryloyl group, a styrenic vinyl group, a vinyl ester group, a maleic acid ester group and maleimide group, and a photoradical polymerization initiator, and a step of forming the insulating wall 4 by irradiating an electromagnetic wave to the photocurable material to cure.

The photocurable material includes at least the polysiloxane compound (component A) having a polymerizable functional group and the photoradical polymerization initiator, but may also include the component M, the component B or the component C described earlier. The detail of these components is as described above.

Examples of the photoradical polymerization initiator include carbonyl compounds, peroxides, azo compounds, sulfur compounds, halogen compounds and metal salts. These polymerization initiators may be used alone or as a mixture. The amount of the polymerization initiator is preferably up to the maximum of 5% by mass with respect to the polymerization mixture.

The photocurable material preferably further contains a polymerization solvent. As the polymerization solvent, any of the organic and inorganic solvents may be used. As examples of the polymerization solvent, water, alcohol-based solvents, glycol ether solvents, ester-based solvents, aliphatic hydrocarbon-based solvents, alicyclic hydrocarbon-based solvents, ketone-based solvents, aromatic hydrocarbon-based solvents and petroleum-based solvents can be used. As the alcohol-based solvents, for example, methyl alcohol, ethyl alcohol, normal propyl alcohol, isopropyl alcohol, normal butyl alcohol, isobutyl alcohol, t-butyl alcohol, t-amyl alcohol, tetrahydrolinalool, ethylene glycol, diethylene glycol, triethylene glycol, tetraethylene glycol, polyethylene glycol, and the like can be used. As the glycol ether-based solvents, methyl cellosolve, ethyl cellosolve, isopropyl cellosolve, butyl cellosolve, propylene glycol monomethyl ether, diethylene glycol monomethyl ether, triethylene glycol monomethyl ether, polyethylene glycol monomethyl ether, ethylene glycol dimethyl ether, diethylene glycol dimethyl ether, triethylene glycol dimethyl ether, polyethylene glycol dimethyl ether, and the like can be used. As the ester-based solvents, ethyl acetate, butyl acetate, amyl acetate, ethyl lactate, methyl benzoate, and the like can be used. As the aliphatic hydrocarbon-based solvents, normal hexane, normal heptane, normal octane, and the like can be used. As the alicyclic hydrocarbon-based solvents, cyclohexane, ethyl cyclohexane, and the like can be used. As the ketone-based solvents, acetone, methyl ethyl ketone and methyl isobutyl ketone, and the like can be used. As the aromatic hydrocarbon-based solvents, benzene, toluene, xylene, and the like can be used. These solvents may be used alone, or two or more types thereof may be mixed and used in combination.

The insulating wall 4 can be formed by irradiating the photocurable material with electromagnetic waves such as ultraviolet rays, visible light or combinations thereof. The electromagnetic wave to be irradiated is preferably an electromagnetic radiation of a wavelength of 200 to 500 nm. Specific examples of the polymerization by electromagnetic wave irradiation include a short time irradiation (typically, not more than 1 hour) with light containing ultraviolet rays, such as light of a mercury lamp or an ultraviolet lamp (for example, FL15BL, manufactured by TOSHIBA CORPORATION).

A preferred method of forming the insulating wall 4 by electromagnetic wave irradiation is as follows. First, a spacer is disposed so as to surround the electrode element 2 on the substrate 1, and a photocurable material is filled in the space surrounded by the spacer. Then, the filled photocurable material is irradiated with an electromagnetic wave after placing a mask which is patterned so as to block the electromagnetic irradiation onto the electrode element 2. Thereafter, by washing away the uncured photocurable material, a hardened insulating wall can be formed only on a portion where the electromagnetic wave has been irradiated, that is, the portion other than the upper portion of the electrode element.

The electrode 10 can also be produced by first placing a mask that is designed to cover a portion on the substrate 1 where the electrode element 2 will be disposed, followed by irradiation with electromagnetic waves, then washing away the uncured photocurable material to thereby form the insulating wall 4, and then placing the electrode elements 2 on the substrate.

It is also possible to further carry out thermal polymerization after the photopolymerization by electromagnetic irradiation, or perform supplementary thermal polymerization prior to the photopolymerization.

The substrate is preferably subjected to plasma ashing before placing the photocurable material, since the surface of the substrate is modified, and adhesion to the insulating wall is further improved.

Figure 2A:
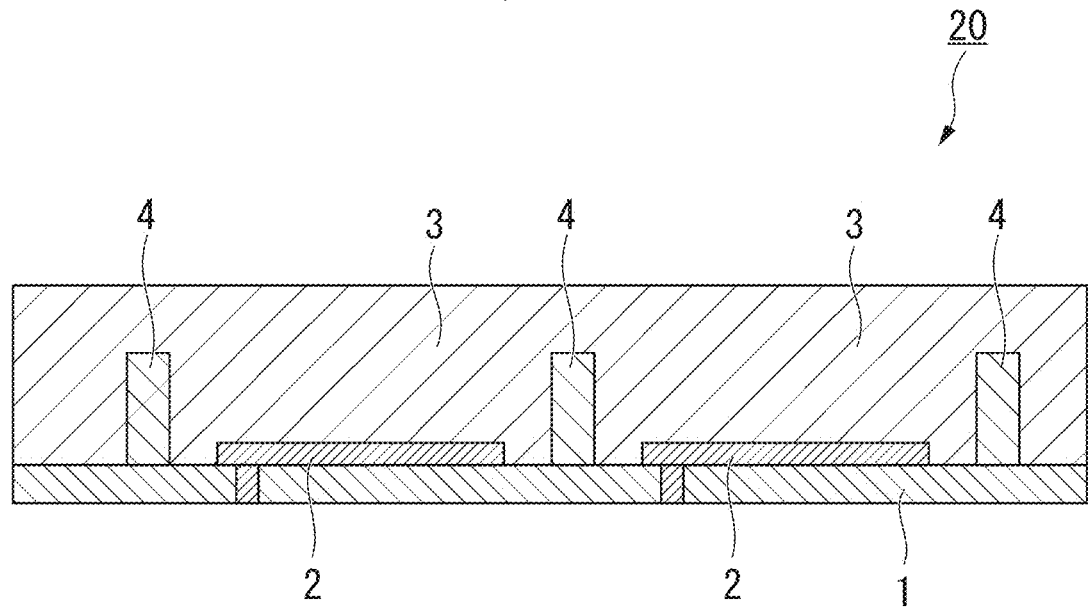
FIG. 2A is a diagram schematically showing the cross-section of an electrode according to an embodiment of the present invention.

The electrode 10 is preferably one having a biological buffer layer 3 formed on the electrode element 2 so as to further prevent the contact between the electrode element 2 and the living body. FIG. 2A is a diagram schematically showing the cross section of an electrode having a biological buffer layer, and FIG. 2B is a schematic perspective view of an electrode having a biological buffer layer.

Figure 2B:
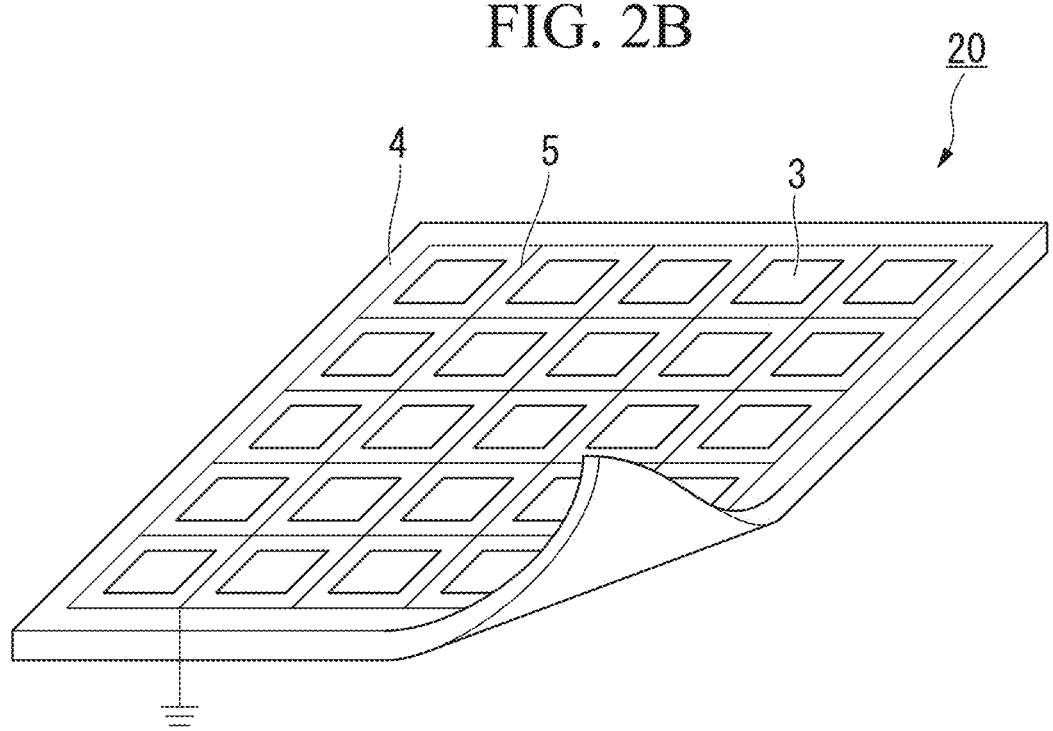
FIG. 2B is a schematic perspective view of an electrode according to an embodiment of the present invention.

An electrode 20 shown in FIGS. 2A and 2B includes, on a substrate 1, a plurality of electrode elements 2 arranged on the same plane, a biological buffer layer 3, and an insulating wall 4 arranged around the electrode elements 2. The biological buffer layer 3 is a layer exhibiting electrical conductivity and capable of transmitting the electrical signals from a living body to the electrode element, and also exhibiting biocompatibility. It is also a layer for suppressing the defense reactions of the living body due to direct contact of the electrode element and the living body. The insulating wall 4 may be provided with a ground wire 5 internally or in the lower portion thereof.

As the biological buffer layer 3, those obtained by uniformly dispersing a conductive material in a hydrophilic gel material, a biocompatible polymer medium, or the like can be used. As the hydrophilic gel material, a variety of high water content gels including hydrogels, such as poly 2-hydroxyethyl methacrylate (also known as: poly-HEMA), silicone hydrogels, polyrotaxane, and polyvinyl alcohol hydrogels are available. As the conductive material, it is possible to use fine metal particles, graphite, carbon black, carbon nanomaterials or the like. Further, for example, a gel-like conductive material (conductive gel) may be used, which is obtained by dispersing a carbon nanomaterial doubly coated with molecules constituting a hydrophilic ionic liquid and a water-soluble polymer in a water-soluble polymer medium, and cross-linking the water-soluble polymer.

Since the biological buffer layer 3 is soft, the contact surface is capable of following the complicated shape of the living body, and the sensitivity of the electrode can be enhanced. In order to achieve the follow-up capability of the contact surface with respect to the surface of the living body with a complex shape at an extremely high level in the laminated structure of the substrate 1 and the biological buffer layer 3, it is important that the substrate has a thickness and Young's modulus sufficient enough to achieve both flexibility and strength, and that the biological buffer layer has Young's modulus comparable to that of the living body and a thickness which follows the contact surface. Therefore, the relationships represented by the following formulae will be suitable conditions: (the thickness of the substrate 1)<(the thickness of the biological buffer layer 3); and (the Young's modulus of the substrate 1)>(the Young's modulus of the biological buffer layer 3).

The Young's modulus of the biological buffer layer 3 may be suitably determined in accordance with the application, but in general, it is preferably from 1 kPa to 100 kPa. Because the Young's modulus of the brain is approximately within this range, by ensuring that the Young's modulus of the biological buffer layer 3 is within this range, it can also be applied to a soft object like a brain with a complex shape.

The thickness of the biological buffer layer 3 is preferably equal to or greater than 0.002 mm and equal to or less than 5 mm. If the thickness of the biological buffer layer 3 is thinner than 0.002 mm, the rigidity of the electrode element cannot be sufficiently reduced, thereby increasing the rigidity of the surface of the biological buffer layer, which is a problem. On the other hand, if the thickness is thicker than 5 mm, there are problems in that the spatial resolution cannot be increased, and the insertion into narrow gaps cannot be conducted.

The height of the insulating wall 4 is preferably about the same as the thickness of the biological buffer layer 3, although it may be slightly higher or lower than the biological buffer layer 3. It is possible to sufficiently prevent leakage of the current even if the height of the insulating wall 4 is slightly lower than the thickness of the biological buffer layer 3. Even if the height of the insulating wall 4 is slightly higher than the thickness of the biological buffer layer 3, since the biological buffer layer 3 can satisfactorily follow a living body by pressing the electrode to the living body, it is possible to sufficiently transmit electrical signals from the living body to the electrode element. The expression "slightly" used herein refers to a range within 30% of the thickness of the biological buffer layer. In general, since strong adhesion cannot be achieved between the biological buffer layer and the electrode element, the biological buffer layer may be peeled off from the substrate. However, by ensuring that both the insulating wall 4 and the biological buffer layer 3 have approximately the same height, the contact surface between the biological buffer layer 3 and the insulating wall 4 is increased, so that an effect of preventing detachment of the biological buffer layer can also be achieved.

The electrode 10 having the biological buffer layer 3 can be produced by further going through a step of laminating the biological buffer layer 3, in addition to the method of producing the electrode 10 described above.

The electrode 10 is a preferred embodiment of the electrode according to the present invention in which a plurality of electrode elements 2 are regularly arranged on the substrate 1, and the insulating wall 4 formed by the polymer described above is formed so as to insulate the plurality of electrode elements 2 from each other. An electrode that includes such a plurality of electrode elements may be referred to as an "electrode array".

Figure 3A:
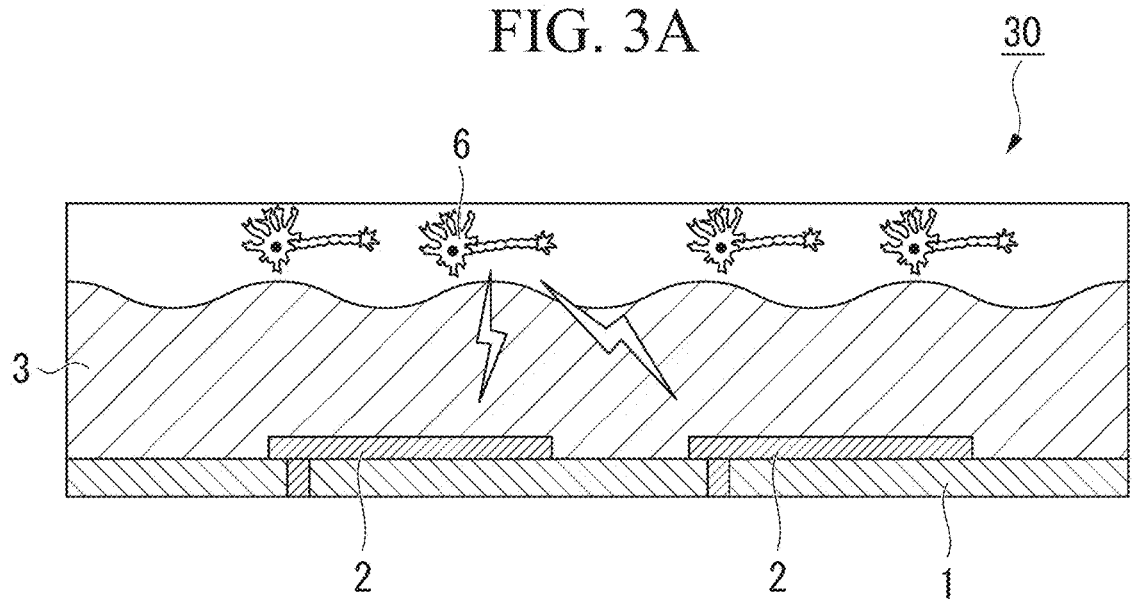
FIG. 3A is a schematic cross-sectional view of an electrode for schematically illustrating the action of an electrode having no insulating wall.
Figure 3B:
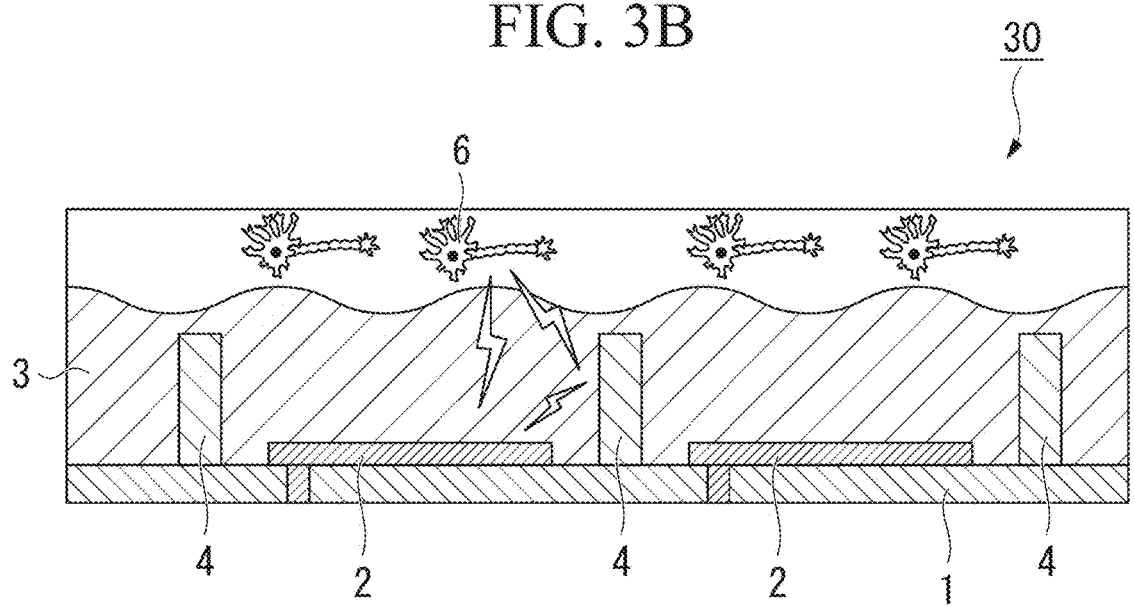
FIG. 3B is a schematic cross-sectional view of an electrode for schematically illustrating the action of an electrode having an insulating wall according to an embodiment of the present invention.

FIG. 3A is a diagram schematically showing the action of an electrode array having no insulating wall, whereas FIG. 3B is a diagram schematically showing the action of an electrode array having an insulating wall according to an embodiment of the present invention. As shown in FIGS. 3A and 3B, electrode arrays are in contact with the living body via the biological buffer layers 3.

As shown in FIG. 3A, in the case of an electrode array 30 having no insulating wall, for example, an electrical signal emitted from a nerve cell 6 diffuses to the periphery in the form of an electric current via the biological buffer layer 3 exhibiting electrical conductivity. Although this electric current is measured most strongly at the electrode element 2 closest to the nerve cell 6, the electric current also leaks out to the electrode elements 2 in the periphery thereof. This phenomenon is known as crosstalk. Therefore, the electrical signal emitted from the nerve cell 6 will be received in a blurred state at the electrode array 30 as a whole, so that the electrode array 30 cannot achieve sufficient spatial resolution.

On the other hand, as shown in FIG. 3B, in the case of an electrode array 20 having an insulating wall 4 in accordance with an embodiment of the present invention, since the insulating wall 4 has an insulating property, diffusion of the electric current to the periphery via the biological buffer layer is inhibited. Therefore, the electrical signal emitted from the nerve cell 6 is received more strongly at the electrode element 2 closest to the nerve cell 6, and leakage to the electrode element 2 in the periphery is prevented. For this reason, the electrode array 20 can exhibit high levels of spatial resolution and sensitivity.

As shown in FIG. 3B, the electrode array is preferably provided with a ground wire 5 inside the insulating wall 4 or in the lower portion of the insulating wall 4. If the amount of electrical signals (amount of electric current) from a living body is large, the insulating wall 4 alone can no longer provide sufficient insulation, and crosstalk occurs. Therefore, by having the ground wire 5 inside the insulating wall 4 or in the lower portion of the insulating wall 4, it is also possible to cut off the electrical signal that has been leaked out through the insulating wall 4, and the crosstalk can be suppressed even further. In other words, it is possible to further enhance the sensitivity of the electrode array 20. Further, the ground wire 5 is not limited as long as it exhibits electrical conductivity, and it is possible to use a metal, indium tin oxide (ITO), or the like.

EXAMPLES

The present invention will be described in more detail below using a series of examples, although the present invention is not limited by these examples.
(Analytical Methods and Evaluation Methods)
(1) Young's Modulus and Tensile Elongation (Fracture Elongation)
A test piece with a width (the smallest part) of 5.0 mm and a length of 14.0 mm was cut out from a film-shaped polymer by using a specific punching die. Using the test piece, a tensile test was carried out using the RTG-1210 Model testing machine (Load Cell UR-10N-D Model) manufactured by Orientec Co., Ltd. The tensile speed was 100 mm/min, and the distance (initial distance) between grips was 5 mm.

Experimental Example 1

A polydimethylsiloxane having methacrylate groups at both ends (FM7726, manufactured by JNC Corporation, mass average molecular weight: 29,000, number average molecular weight: 26,000) (28 parts by mass) as the component A, a polydimethylsiloxane having a methacrylate group at one end (FM0721, manufactured by JNC Corporation, molecular weight: 5,000) (7 parts by mass) as the component M, trifluoroethyl acrylate (Viscoat 3F, manufactured by Osaka Organic Chemical Industry) (59.5 parts by mass) as the component B, and 2-ethylhexyl acrylate (2EHA, manufactured by Tokyo Chemical Industry Co., Ltd.) (5.0 parts by mass), Irgacure (IC, registered trademark) 819 (manufactured by Ciba Specialty Chemicals, 0.5 parts by mass) and t-amyl alcohol (TAA, manufactured by Tokyo Chemical Industry Co., Ltd., 10 parts by mass) as other components were mixed and stirred. As a result, a uniform transparent photocurable material was obtained.

The photocurable material was placed in a test tube, and deaeration was carried out by reducing the pressure to 20 Torr (27 hPa) while stirring with a touch mixer. Then the pressure was returned to atmospheric pressure with argon gas. This operation was repeated three times.

A glass plate was prepared as a substrate. An OHP sheet was placed on the substrate, and a spacer having a thickness of 0.5 mm was further installed. The photocurable material was filled in a region surrounded by the spacer. The photocurable material was cured by being exposed to UV rays through the glass plate. The UV exposure at this time was carried out using a Light box (W532×D450×H100 mm) manufactured by Sunhayato Corporation and the Black light FL15BL (trade name) manufactured by NEC Corporation with a UV wavelength of 300 nm to 400 nm as a light source.

As a result, a film-shaped polymer was formed on the glass substrate. The Young's modulus and the tensile elongation of the resulting polymer are as shown in Table 1, which indicated high flexibility and excellent mechanical strength.

Experimental Examples 2 to 8

A film-shaped polymer was formed in the same manner as in Experimental Example 1 with the exception that the composition was changed as shown in Table 1. The Young's modulus and the tensile elongation of the resulting polymer were as shown in Table 1.

Experimental Example 9

A polyethylene glycol #200 dimethacrylate (4G, manufactured by Shin-Nakamura Chemical Co., Ltd.) (1 part by mass) as a crosslinking agent, FM7726 (mass average molecular weight: 29,000, number average molecular weight: 26,000) (28 parts by mass) as the component A, FM0721 (molecular weight: 5,000) (7 parts by mass) as the component M, Viscoat 3F (59.5 parts by mass) as the component B, and 2EHA (5.0 parts by mass), IC 819 (0.5 parts by mass) and TAA (10 parts by mass) as other components were mixed and stirred. As a result, a uniform transparent photocurable material was obtained. Apart from that, the operation was carried out in the same manner as in Experimental Example 1 to form a film-shaped polymer. The Young's modulus and the tensile elongation of the resulting polymer were as shown in Table 1.

Experimental Examples 10 and 11

A film-shaped polymer was formed in the same manner as in Experimental Example 9 with the exception that the composition was changed as shown in Table 1. The Young's modulus and the tensile elongation of the resulting polymer were as shown in Table 1.

Experimental Examples 12 and 13

A film-shaped polymer was formed in the same manner as in Experimental Example 1 with the exceptions that trimethylolpropane trimethacrylate (TMPTM, manufactured by Wako Pure Chemical Industries, Ltd.) was used as a crosslinking agent, and that the composition was changed as shown in Table 1. The Young's modulus and the tensile elongation of the resulting polymer were as shown in Table 1.

Experimental Examples 14 to 21

A film-shaped polymer was formed in the same manner as in Experimental Example 1 with the exceptions that a dimethyl silicone oil methacryl-modified at both ends was used as a crosslinking agent (FM7711, manufactured by JNC Corporation, molecular weight: 10,000), and that the compositions were changed as shown in Tables 1 and 2. The Young's modulus and the tensile elongation of the resulting polymer were as shown in Tables 1 and 2.

Experimental Examples 22 and 23

A film-shaped polymer was formed in the same manner as in Experimental Example 1 with the exception that the composition was changed as shown in Table 2. The Young's modulus and the tensile elongation of the resulting polymer were as shown in Table 2.

Experimental Example 24

Methyl methacrylate (MMA, manufactured by Tokyo Chemical Industry Co., Ltd.) (99.5 parts by mass), IC 819 (0.5 parts by mass) and TAA (10 parts by mass) were mixed and stirred, thereby obtaining a photocurable material. Apart from that, the operation was carried out in the same manner as in Experimental Example 1 to form a film-shaped polymer on a glass substrate. The Young's modulus and the tensile elongation of the resulting polymer were as shown in Table 2, indicating that the resulting polymer was very hard with no elasticity.

Experimental Example 25

IC 819 (0.5 parts by mass) and TAA (20 parts by mass) were mixed. Sylgard 184 (Sigma-Aldrich Japan KK: registered trademark) (99.5 parts by mass) which is a polysiloxane compound having a vinyl ether group represented by the following formula (S1) was added thereto and stirred, thereby obtaining a photocurable material. Apart from that, the operation was carried out in the same manner as in Experimental Example 1, followed by UV exposure. Although the exposure was continued for 30 minutes, a film-shaped polymer could not be obtained.

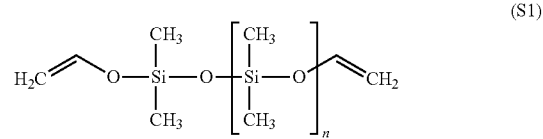

(S1)

Experimental Example 26

The operation was carried out in the same manner as in Experimental Example 25 with the exceptions that 2-hydroxy-2-methyl propiophenone (manufactured by Sigma-Aldrich Japan K.K., CAS number: 7473-98-5) (4.5 parts by mass) was used as a photopolymerization initiator, and that the composition was changed as shown in Table 1, followed by UV exposure. Although the exposure was continued for 30 minutes, a film-shaped polymer could not be obtained.

Experimental Example 27

The operation was carried out in the same manner as in Experimental Example 26 with the exception that the composition was changed as shown in Table 2, followed by UV exposure. Although the exposure was continued for 30 minutes, a film-shaped polymer could not be obtained.

TABLE 1

| | | | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 | Ex. 13 | Ex. 14 |
|---|---|---|---|---|---|---|---|---|---|---|---|---|---|---|---|---|
| Component A | FM7726 | Parts | 28.0 | 35.6 | 51.6 | 67.6 | 24.2 | 38.2 | 52.2 | 69.7 | 28.0 | 69.7 | 69.7 | 28.0 | 69.7 | 28.0 |
| Component M | FM0721 | by | 7.0 | 8.9 | 12.9 | 16.9 | 10.4 | 16.4 | 22.4 | 29.9 | 7.0 | 29.9 | 29.9 | 7.0 | 29.9 | 7.0 |
| Component B | Viscoat 3F | mass *1 | 59.5 | 50 | 30 | 10 | 50 | 30 | 10 | — | 59.5 | — | — | 59.5 | — | 59.5 |
| | 2EHA | | 5 | 5 | 5 | 5 | 5 | 5 | 5 | — | 5 | — | — | 5 | — | 5 |
| | MMA | | — | — | — | — | — | — | — | — | — | — | — | — | — | — |
| | Sylgard 184 | | — | — | — | — | — | — | — | — | — | — | — | — | — | — |
| Photopoly- | IC819 | | 0.5 | 0.5 | 0.5 | 0.5 | 0.5 | 0.5 | 0.5 | 0.5 | 0.5 | 0.5 | 0.5 | 0.5 | 0.5 | 0.5 |
| merization initiator | HMPP | | — | — | — | — | — | — | — | — | — | — | — | — | — | — |
| Crosslinking | 4G | | — | — | — | — | — | — | — | — | 1 | 1 | 2.5 | — | — | — |
| agent | TMPTM | | — | — | — | — | — | — | — | — | — | — | — | 1 | 1 | — |
| | FM7711 | | — | — | — | — | — | — | — | — | — | — | — | — | — | 1 |
| Poly- merization solvent | TAA | | 10 | 10 | 10 | 10 | 10 | 10 | 10 | 20 | 10 | 20 | 20 | 10 | 20 | 10 |
| Young's modulus (kPa) | | | 480 | 500 | 540 | 460 | 415 | 425 | 370 | 90 | 615 | 175 | 155 | 420 | 245 | 500 |
| Tensile elongation (%) | | | 1060 | 990 | 605 | 400 | 1210 | 800 | 540 | 745 | 650 | 420 | 505 | 620 | 560 | 700 |

*1 The sum of the mass of the components obtained by excluding the crosslinking agent and the polymerization solvent from the photocurable material is defined as 100 parts by mass.

TABLE 2

| | | | Ex. 15 | Ex. 16 | Ex. 17 | Ex. 18 | Ex. 19 | Ex. 20 | Ex. 21 | Ex. 22 |
|---|---|---|---|---|---|---|---|---|---|---|
| Component A | FM7726 | Parts | 28.0 | 28.0 | 28.0 | 69.7 | 69.7 | 69.7 | 69.7 | 99.5 |
| Component M | FM0721 | by | 7.0 | 7.0 | 7.0 | 29.9 | 29.9 | 29.9 | 29.9 | — |
| Component B | Viscoat 3F | mass *1 | 59.5 | 59.5 | 59.5 | — | — | — | — | — |
| | 2EHA | | 5 | 5 | 5 | — | — | — | — | — |
| | MMA | | — | — | — | — | — | — | — | — |
| | Sylgard 184 | | — | — | — | — | — | — | — | — |
| Photopoly- | IC819 | | 0.5 | 0.5 | 0.5 | 0.5 | 0.5 | 0.5 | 0.5 | — |
| merization initiator | HMPP | | — | — | — | — | — | — | — | 0.5 |
| Crosslinking | 4G | | — | — | — | — | — | — | — | — |
| agent | TMPTM | | — | — | — | — | — | — | — | — |
| | FM7711 | | 3 | 5 | 20 | 1 | 3 | 5 | 20 | — |

TABLE 2-continued

| | | | | | | | | | |
|---|---|---|---|---|---|---|---|---|---|
| Polymerization solvent | TAA | 10 | 10 | 10 | 20 | 20 | 20 | 20 | 10 |
| Young's modulus (kPa) | | 670 | 730 | 1000 | 70 | 185 | 250 | 450 | 380 |
| Tensile elongation (%) | | 500 | 390 | 150 | 745 | 655 | 360 | 375 | 420 |

| | | | | Ex. 23 | Ex. 24 | Ex. 25 | Ex. 26 | Ex. 27 |
|---|---|---|---|---|---|---|---|---|
| Component A | FM7726 | Parts by mass *1 | | 35.0 | — | — | — | — |
| Component M | FM0721 | | | — | — | — | — | — |
| Component B | Viscoat 3F | | | 59.5 | — | — | — | — |
| | 2EHA | | | 5 | — | — | — | — |
| | MMA | | | — | 99.5 | — | — | — |
| | Sylgard 184 | | | — | — | 99.5 | 99.5 | 100 |
| Photopolymerization initiator | IC819 | | | 0.5 | 0.5 | 0.5 | — | — |
| | HMPP | | | — | — | — | 4.5 | 4.5*2 |
| Crosslinking agent | 4G | | | — | — | — | — | — |
| | TMPTM | | | — | — | — | — | — |
| | FM7711 | | | — | — | — | — | — |
| Polymerization solvent | TAA | | | 10 | 10 | 20 | — | — |
| Young's modulus (kPa) | | | | 840 | Unmeasurable | Unmeasurable | Unmeasurable | Unmeasurable |
| Tensile elongation (%) | | | | 480 | Unmeasurable | Unmeasurable | Unmeasurable | Unmeasurable |

*1 The sum of the mass of the components obtained by excluding the crosslinking agent and the polymerization solvent from the photocurable material is defined as 100 parts by mass.
*2 For Reference Example 25, the sum of the mass of the components obtained by also exluding the photopolymerization initiator from the photocurable material is defined as 100 parts by mass.

Example 1

A polyimide film having a film thickness of 12 μM was prepared as a substrate. Gold was deposited on the polyimide film through a mask to form 64 electrode elements having a square shape of 7 mm×7 mm in 1 mm intervals in an array of 8 vertical columns×8 horizontal rows.

Next, a spacer having a thickness of 1 mm was installed around the substrate, and the region surrounded by the spacer was filled with the photocurable material described in Experimental Example 1. A mask in which a line having a width of 1 mm was formed in a grid-like manner with 7 mm intervals was arranged thereon so that the line was matched with the grid-like portion on the substrate where no electrode element was formed, and the photocurable material was cured by UV exposure. The UV exposure at this time was carried out using the Light box (W532×D450×H100 mm) manufactured by Sunhayato Corporation and the Black light FL15BL (trade name) manufactured by NEC Corporation with a UV wavelength of 300 nm to 400 nm as a light source. Then, the photocurable material in the unexposed portion was rinsed with isopropyl alcohol, thereby developing an insulating wall with a grid-like shape. Thereafter, the insulating wall was subjected to UV exposure and allowed to postcure even further.

Figure 4:
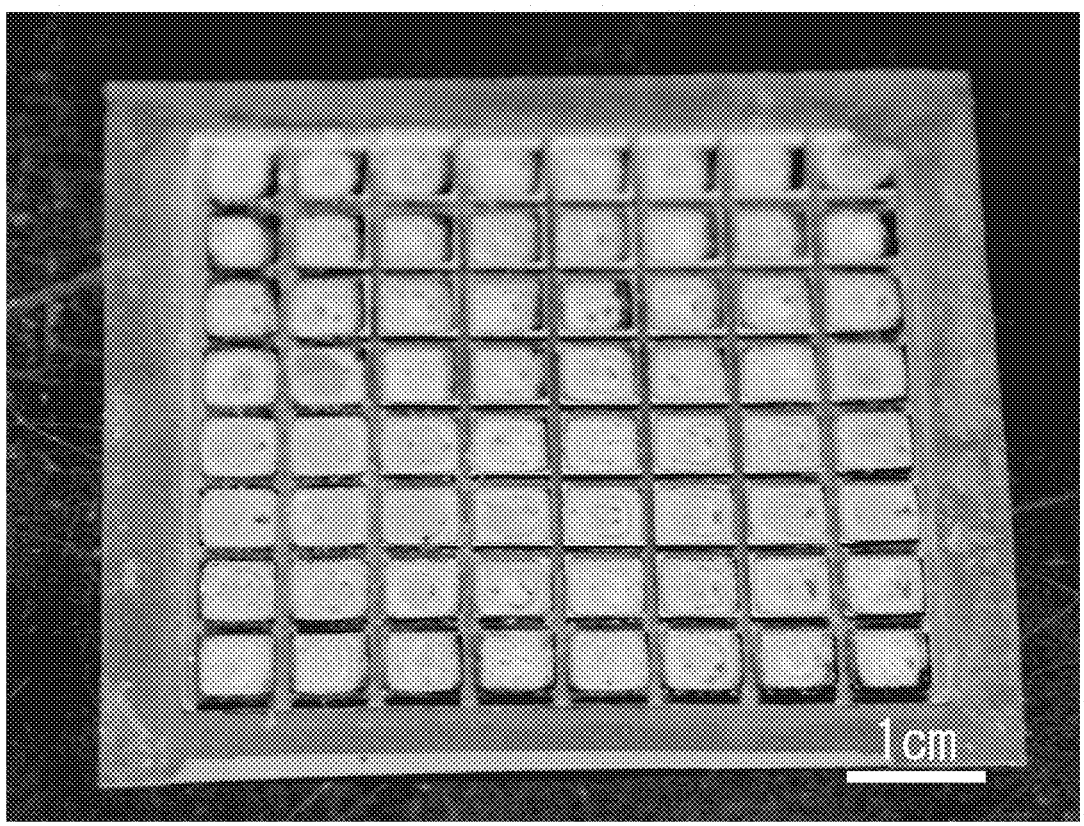
FIG. 4 is a plan view photograph of an electrode prepared in Example 1 of the present invention.

As a result, an insulating wall with a grid-like shape composed of 8 rows and 8 columns of cells, each having a size of 7 mm×7 mm, was formed on the substrate. The height of the insulating wall in this case was 1 mm. FIG. 4 is a plan view photograph of the electrode (electrode array) prepared in the present Example.

Example 2

As a biological buffer layer, a composition formed by dispersing a carbon nanotube covered with molecules constituting N,N-diethyl-N-methyl-N-(2-methoxyethyl) ammonium tetrafluoroborate ($DEMEBF_4$) in polyrotaxane was prepared as follows.

30 mg of carbon nanotube (VGCF-X, manufactured by Showa Denko K.K., length: 3 μm, diameter: 15 nm) and 60 mg of N,N-diethyl-N-methyl-N-(2-methoxyethyl) ammonium tetrafluoroborate ($DEMEBF_4$) which was a hydrophilic ionic liquid were mixed, and the resulting mixture was stirred in deionized water at 25° C. for 1 week at a rotational speed equal to or greater than 700 rpm using a magnetic stirrer. The resulting suspension was treated by a high-pressure jet mill homogenizer; (60 MPa; Nano jet pal, JN 10, Jokoh Co., Ltd.), thereby obtaining a black substance. After rinsing the resulting solution containing a CNT gel with a physiological saline solution, 1 mg of a photopolymerization initiator (IC2959, manufactured by Nagase & Co., Ltd.) and 1,000 mg of polyrotaxane gel ("photocrosslinkable slide-ring gel", manufactured by Advanced Softmaterials Inc.) were mixed, thereby producing the composition described above.

The gel-like material was filled into a cell surrounded by the insulating wall of an electrode prepared in the same manner as in Example 1. Then, polyrotaxane was cross-linked by UV exposure, and the carbon nanotube covered with the molecules constituting $DEMEBF_4$ was dispersed in the polyrotaxane medium, thereby producing a biological buffer layer in which the polyrotaxane was cross-linked. The UV exposure at this time was carried out using the Light box (W532×D450×H100 mm) manufactured by Sunhayato Corporation and the Black light FL15BL (trade name) manufactured by NEC Corporation with a UV wavelength of 300 nm to 400 nm as a light source. The thickness of the biological buffer layer at this time was 1 mm which was the same as the height of the insulating wall.

Comparative Example 1

The operation was carried out in the same manner as in Example 1 with the exception that the photocurable material described in Experimental Example 25 was used, followed by UV exposure. Although the UV exposure was conducted for 30 minutes and the photocurable material in the unexposed portion was washed, the insulating wall was not formed.

Comparative Example 2

The operation was carried out in the same manner as in Example 1 with the exception that the photocurable material described in Experimental Example 26 was used, followed by UV exposure. Although the UV exposure was conducted for 30 minutes and the photocurable material in the unexposed portion was washed, the insulating wall was not formed.

Comparative Example 3

A spacer having a thickness of 1 mm was installed around the substrate, and the region surrounded by the spacer was filled with the composition described in Example 2 which was cured by UV exposure, thereby forming a biological buffer layer. The insulating wall was not formed.

(Results of Electrode Evaluation)

Figure 5A:
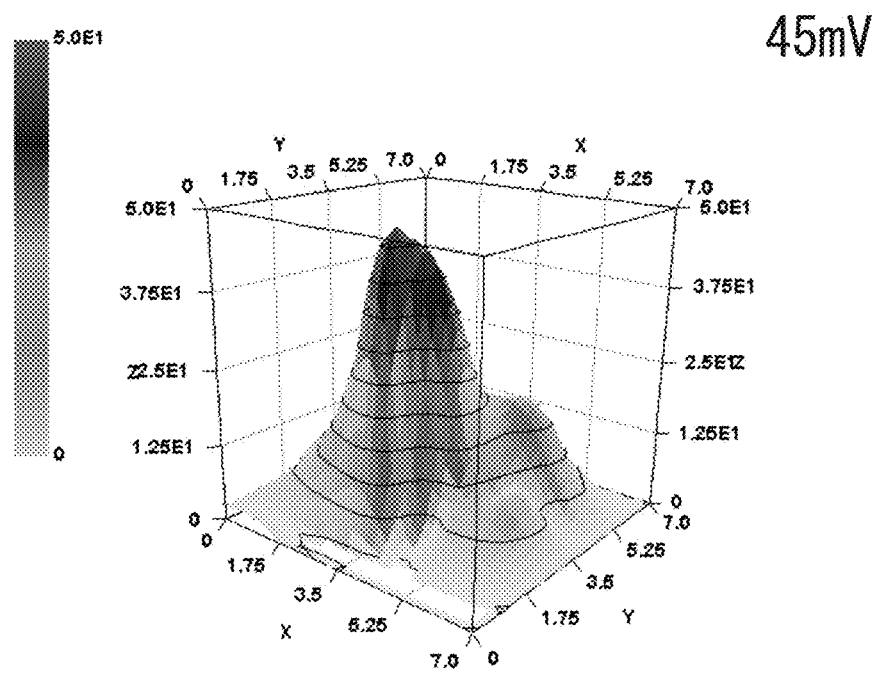
FIG. 5A is a graph showing the output result, when an input voltage of 100 mV was applied onto a certain point in an electrode array in Example 1 of the present invention, which was measured by the electrode opposing the location where the input voltage was applied.
Figure 5B:
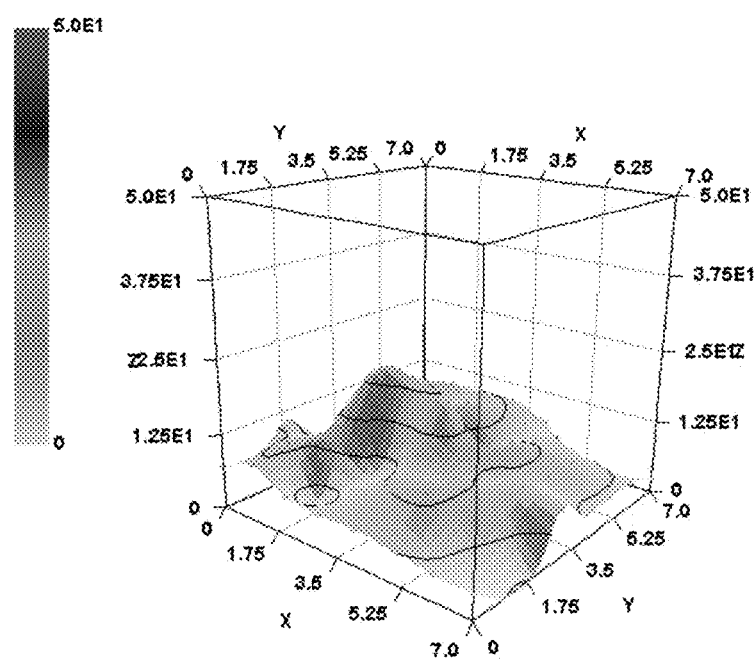
FIG. 5B is a graph showing the output result, when an input voltage of 100 mV was applied onto a certain point in an electrode array in Comparative Example 3 of the present invention, which was measured by the electrode opposing the location where the input voltage was applied.

FIG. 5A is a graph showing the output result, when an input voltage of 100 mV was applied onto a certain point in an electrode array in an Example, which was measured by the electrode opposing the location where the input voltage was applied. FIG. 5B is a graph showing the output result, when an input voltage of 100 mV was applied onto a certain point in an electrode array in an Example, which was measured by the electrode opposing the location where the input voltage was applied. In these graphs, the vertical axis indicates the output voltage, whereas the XY axes indicate the position coordinates. The XY coordinate in the graph has a size of 7 mm×7 mm, which is the size of a single cell surrounded by the insulating wall in Example 1, and the output result is an output result measured by one electrode element opposing the point where the input voltage was applied.

As a result, it is clear that while the electrode array of Example 1 shows an output result of 45 mV with respect to the input voltage of 100 my, the electrode array of Comparative Example 3 only shows an output result of 23 mV with respect to the input voltage of 100 mV. In addition, as is also apparent from the graph, it is clear that the electrode array of Example 1 showed a detection result with a higher peak, indicating a higher sensitivity of the electrode array.

Figure 6A:
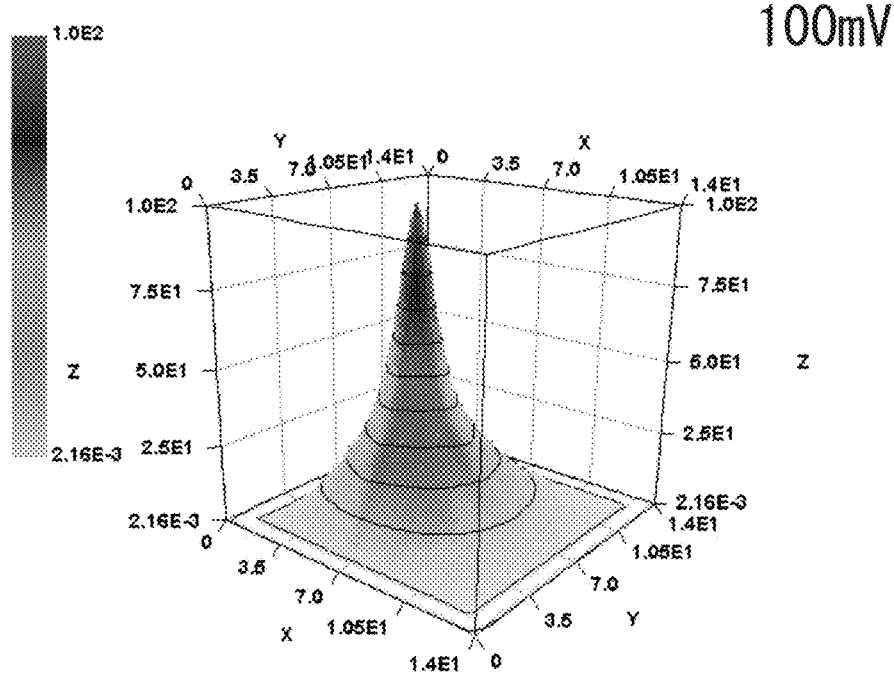
FIG. 6A is a graph simulating the output result, when an input voltage of 100 mV was applied onto a certain point in an electrode array in Example 1 of the present invention, which was measured by the electrode opposing the location where the input voltage was applied.
Figure 6B:
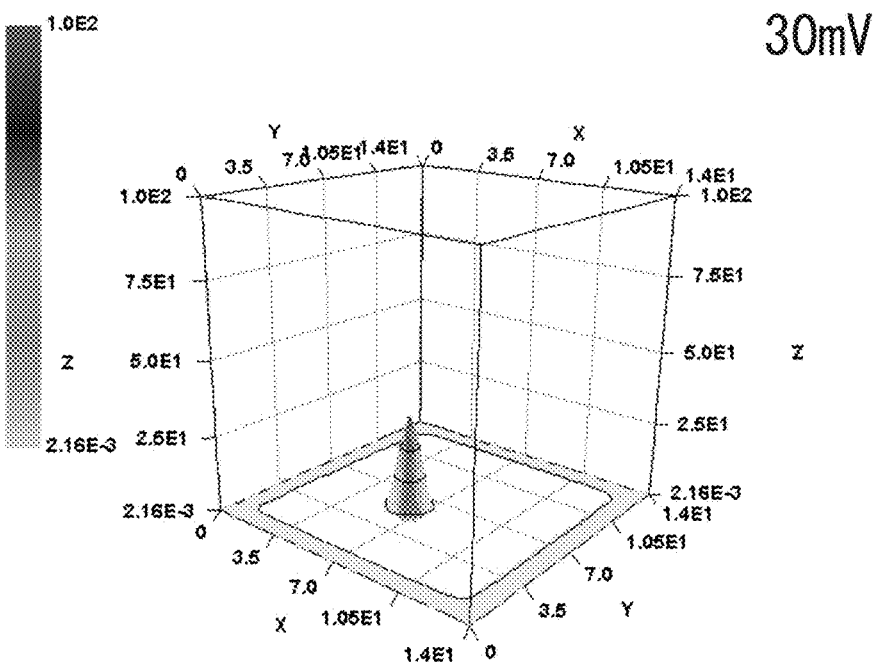
FIG. 6B is a graph simulating the output result, when an input voltage of 100 mV was applied onto a certain point in an electrode array in Comparative Example 3 of the present invention, which was measured by the electrode opposing the location where the input voltage was applied.

FIG. 6A is a graph simulating the output result, when an input voltage of 100 mV was applied onto a certain point in an electrode array in an Example, which was measured by the electrode opposing the location where the input voltage was applied. FIG. 6B is a graph simulating the output result, when an input voltage of 100 mV was applied onto a certain point in an electrode array in a Comparative Example, which was measured by the electrode opposing the location where the input voltage was applied. The vertical axis indicates the output voltage, whereas the XY axes indicate the position coordinates.

Simulation was performed by electrostatic field analysis using the finite difference method. The size of the finite difference grid was a cube with a side of 1 mm, with 58×58 grids in a direction parallel to the substrate, and one grid in the thickness direction perpendicular to the substrate.

As a result, it is clear that while the electrode array of Example 1 shows an output result of 100 mV with respect to the input voltage of 100 my, the electrode array of Comparative Example 3 only shows an output result of 30 mV with respect to the input voltage of 100 mV. In addition, as is also apparent from the graph, it is clear that the electrode array of Example 1 showed a detection result with a higher peak, indicating a higher sensitivity.

REFERENCE SIGNS LIST

1: Substrate; 2: Electrode element; 3: Biological buffer layer; 4: Insulating wall; 5: Ground wire; 10: Electrode; 20, 30: Electrode (electrode array)

The invention claimed is:

1. An electrode configured for detecting electrical signals from biological tissue comprising, on a substrate,
   an electrode element; and
   an insulating wall formed around the electrode element, constituted of a polysiloxane compound (component A) having, per molecule, two or more functional groups selected from the group consisting of a (meth)acryloyl group, a styrenic vinyl group, a vinyl ester group, a maleic acid ester group and a maleimide group, and formed from a polymer obtained by reaction of the functional groups.

2. The electrode according to claim 1,
   wherein the component A is a compound having a structure represented by the following general formula (A1);

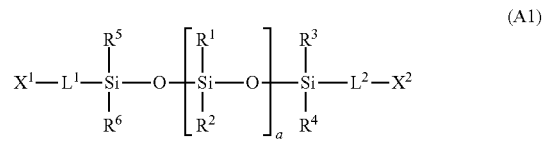

wherein each of $X^1$ and $X^2$ independently represents a functional group selected from the group consisting of a (meth)acryloyl group, a styrenic vinyl group, a vinyl ester group, a maleic acid ester group and a maleimide group;

each of $R^1$ to $R^6$ independently represents a substituent group selected from hydrogen, an alkyl group of 1 to 20 carbon atoms, a phenyl group, and a fluoroalkyl group of 1 to 20 carbon atoms;

each of $L^1$ and $L^2$ independently represents a divalent group; and

"a" is a number of siloxane repeating units represented by an integer of 1 to 3,000.

3. The electrode according to claim 1, wherein a number average molecular weight of the component A is at least 6,000.

4. The electrode according to claim 1,
   wherein the polymer is a copolymer obtained by copolymerizing the component A and a polysiloxane compound (component M) having, per molecule, one functional group selected from the group consisting of a (meth)acryloyl group, a styrenic vinyl group, a vinyl ester group, a maleic acid ester group and a maleimide group.

5. The electrode according to claim 4,
   wherein the component M is a compound having a structure represented by the following general formula (M1);

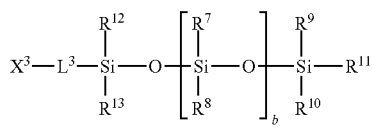

(M1)

wherein $X^3$ represents a functional group selected from the group consisting of a (meth)acryloyl group, a styrenic vinyl group, a vinyl ester group, a maleic acid ester group and a maleimide group; each of $R^7$ to $R^{13}$ independently represents a substituent group selected from hydrogen, an alkyl group of 1 to 20 carbon atoms, a phenyl group, and a fluoroalkyl group of 1 to 20 carbon atoms; $L^3$ represents a divalent group; and "b" is a number of siloxane repeating units represented by an integer of 0 to 1,400.

6. The electrode according to claim 1,
wherein the polymer is a copolymer obtained by copolymerizing the component A and a compound (component B) having a fluoroalkyl group and one or more functional groups, per molecule, selected from the group consisting of a (meth)acryloyl group, a styrenic vinyl group, a vinyl ester group, a maleic acid ester group and a maleimide group.

7. The electrode according to claim 6, wherein the component B is a (meth)acrylic acid fluoroalkyl ester.

8. The electrode according to claim 1,
wherein a plurality of the electrode elements are arranged on the substrate, and
the insulating wall is formed so as to insulate the plurality of electrode elements from each other.

9. The electrode according to claim 1, wherein the insulating wall is formed by polymerizing the component (A) by electromagnetic wave irradiation.

10. The electrode according to claim 1,
wherein the component A is a compound having a structure represented by the following general formula (A1);

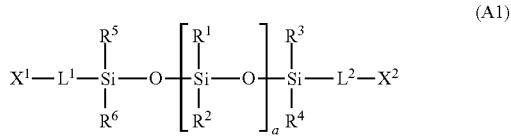

(A1)

wherein both of $X^1$ and $X^2$ are a (meth)acryloyl group;
each of $R^1$ to $R^6$ independently represents a substituent group selected from hydrogen, an alkyl group of 1 to 20 carbon atoms, a phenyl group, and a fluoroalkyl group of 1 to 20 carbon atoms;
each of $L^1$ and $L^2$ independently represents a divalent group; and
"a" is a number of siloxane repeating units represented by an integer of 1 to 3,000.

11. A method for manufacturing an electrode configured for detecting electrical signals from biological tissue, comprising:
a step of placing an electrode element on a substrate;
a step of placing, around the electrode element, a photocurable material including a polysiloxane compound (component A) having, per molecule, two or more functional groups selected from the group consisting of a (meth)acryloyl group, a styrenic vinyl group, a vinyl ester group, a maleic acid ester group and maleimide group, and a photoradical polymerization initiator; and
a step of forming the insulating wall by irradiating an electromagnetic wave to the photocurable material to cure.

* * * * *